US006979698B1

(12) United States Patent
Sandberg et al.

(10) Patent No.: US 6,979,698 B1
(45) Date of Patent: *Dec. 27, 2005

(54) METHOD OF TREATING COGNITIVE DEFICITS IN LEARNING AND MEMORY

(75) Inventors: Paul R. Sandberg, Spring Hill, FL (US); Roland D. Shytle, Lutz, FL (US); Archie A. Silver, Tampa, FL (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/526,403

(22) Filed: Mar. 15, 2000

Related U.S. Application Data

(63) Continuation-in-part of application No. 09/461,087, filed on Dec. 14, 1999, now abandoned, which is a continuation-in-part of application No. 09/198,882, filed on Nov. 23, 1998, now Pat. No. 6,034,079, which is a continuation-in-part of application No. PCT/US98/16634, filed on Aug. 11, 1998, which is a continuation-in-part of application No. PCT/US97/20689, filed on Nov. 7, 1997, which is a continuation-in-part of application No. 08/935,364, filed on Sep. 22, 1997, now abandoned.

(60) Provisional application No. 60/055,234, filed on Aug. 11, 1997.

(51) Int. Cl.$^7$ ............................................. A61K 31/13
(52) U.S. Cl. ....................................... 514/661; 514/660
(58) Field of Search ................................. 514/661, 879

(56) References Cited

U.S. PATENT DOCUMENTS

| | | | | |
|---|---|---|---|---|
| 2,831,027 A | | 4/1958 | Pfister, III et al. .......... 260/563 |
| 2,894,987 A | | 7/1959 | Gustav et al. ............... 260/563 |
| 3,148,118 A | | 9/1964 | Thesing et al. ............... 167/65 |
| 3,164,601 A | | 1/1965 | Thesing et al. .......... 260/294.7 |
| 4,837,218 A | | 6/1989 | Olney ........................ 514/646 |
| 4,891,380 A | | 1/1990 | Williams et al. ............. 514/353 |
| 5,204,470 A | * | 4/1993 | Cliffe ........................ 546/126 |
| 5,554,610 A | | 9/1996 | Williams et al. ......... 514/223.2 |
| 5,574,052 A | | 11/1996 | Rose et al. ................. 514/343 |
| 5,583,140 A | | 12/1996 | Bencherif et al. .......... 514/299 |
| 5,691,365 A | * | 11/1997 | Crooks et al. ............... 514/343 |
| 5,859,004 A | | 1/1999 | Olesen ........................ 514/214 |
| 6,734,215 B2 | * | 5/2004 | Shytle et al. ................ 514/661 |

FOREIGN PATENT DOCUMENTS

EP 0 537 993 A1 4/1993

OTHER PUBLICATIONS

Suzuki et al. "Mecamylamine-precipitated nicotine-withdrawal aversion in rats." European Journal of Pharmacology, 1996, vol. 314, No. 3, pp. 281-284.*
Hayashi, E., et al., "Comparative studies on anti-nicotinic action of hexamethonium, mecamylamine and adenosine in the guinea pig isolated ileum," *Japan J. Pharmacol*, 27: 659-665 (1997).
Sanberg, P.R., et al., "Nicotine for the Treatment of Tourette's Syndrome," *Pharmacol. Ther.* 74(1): 21-25 (1997).
Suchocki, J.A., et al., "Synthesis of 2-exo-and 2-end-mecamylamine analogs. Structure-activity relationships for nicotinic antagonism in the central nervous system," *Journal of Medicinal Chemistry*, 34: 1003-1010 (1991).
European Patent Application No. 98 93 9328.5, Supplementary European Search Report issued Dec. 3, 2003.
Ballivet, et al., "Nicotine Acetylcholine . . . elegans," JMB., 2296, pp. 261-269 (1996).
Banerjee, et al., "[3H]Mecamylamine Binding to Rat Brain Membranes," *Biochemical Pharmacology*, vol. 40, No. 9, pp. 2105-2110 (1990).
Bianchi, C. and L. Tomasi, "Central nervous system and autonomic nervous system effects of amantadine and of some standard anti-Parkinson drugs," *Pharmacology*, 10(4): 226-237 (1973).
Bruun, R.D. and C.L. Budman, "Risperidone as a treatment for Tourette's syndrome," *J.Clin. Psychiatry*, 57(1):29-31 (1996).
Emerich, et al., "Nicotine . . . Locomotor Hypoactivity," *Pharm. Biochem. & Behav.*, vol. 38, pp. 875-880 (1991).
Emerich, et al., Nicotine . . . of Haloperidol, Psychopharm. Bulletin., vol. 27(3): 385-390 (1991).
Erdmann, R., "Nicotine in neuropsychiatric movement disorders," *Fortschr Neurol Psychiatr.*, 64(9): 362-366 (1996).
Freund, R.K., et al., "Nicotine effects in mouse hippocampus are blocked by mecamylamine, but not other nicotinic antagonists," *Brain Res.*, 511(2): 187-191 (1990).
Ghaemi, S.N., et al., "Acute treatment of bipolar disorder with adjunctive risperidone in outpatients," *Can. J. Psychiatry*, 42(2): 196-199 (1997).
Green, M.F., et al., "Does Risperidone Improve Verbal Working Memory in Treatment-Resistant Schizophrenia?" *American Journal of Psychiatry*, 154(6): 799-804 (1997).
Hsu, W., "Toxicity and Drug Interactions of Levamisole," *HAVMA*, vol. 176, No. 10, pp. 1166-1169 (May 1980).

(Continued)

*Primary Examiner*—Sreeni Padmanabhan
*Assistant Examiner*—Jennifer Kim
(74) *Attorney, Agent, or Firm*—Womble Carlyle Sandridge & Rice, PLLC (57) ABSTRACT

The treatment of learning, memory, and age-related memory disorders includes administration of a nicotine antagonist. The preferred nicotine antagonists are mecamylamine, a mecamylamine analog, or a mecamylamine stereoisomer. The effective amount of the nicotine antagonist is 0.005–1.00 mg/kg/day. Alternatively, the method utilizes a partial nicotine agonist.

70 Claims, 1 Drawing Sheet

OTHER PUBLICATIONS

Ivanová, S. and A. J. Greenshaw, "Nicotine-induced decreases in VTA electrical self-stimulation thresholds: blockade by haloperidol and mecamylamine but not scopolamine or ondansetron," *Psychopharmacology*, 134(2): 187-192 (1997).

Jankovic, J. and H. Rohaidy, "Motor, behavior and pharmacologic findings in Tourette's Syndrome," *Can. J. Neurol. Sci.*, 14(3 Suppl.): 541-546 (1987).

Jolles, J., et al., "Cognitive Impairment in Elderly People," *Drugs & Aging*, 7(6): 459-479 (1995).

*The Lancet*, "Nicotine Gum & Haloperidol in Tourette's Syndrome," p. 592 (Mar. 12, 1998).

*The Lancet*, "Transdermal nicotine patch . . . in Tourette's Syndrome," vol. 342, p. 182 (Jul. 17, 1993).

Levin, E. D. and D. Torry, "Acute and chronic nicotine effects on working memory in aged rats," *Psychopharmacology*, 123: 88-97 (1996).

Lindström, E., et al., "Efficacy and safety of risperidone in the long-term treatment of patients with schizophrenia," *Clin. Ther.* 17(3): 402-412 (1995).

Lombroso, P.J., et al., "Risperidone treatment of children and adolescents with chronic tic disorders: a preliminary report," *J. Am. Acad. Child Adolesc. Psychiatry*, 34(9): 1147-1152 (1995).

Lomboros, P.J., et al., "Risperidone treatment of children and adolescents with chronic tic disorders: a preliminary report," *J. Am. Acad. Child Adolsec. Psychiatry*, 35 (3): 394 (1966).

McConville, et al., "The Effects . . . in Tourette's Disorder," *Biol. Psychiatry*, vol. 31 (8): 832-840 (1992).

McConville, et al., "Nicontine . . . in Tourette's Syndrome," *Amer. J. Psychiatry*, 148(6): 793-794 (Jun. 1991).

*Pharmacol Ther.*, "Nicotine for the Treatment of Tourette's Syndrome," vol. 74, No. 1, pp. 21-25 (1997).

*Psychopharmacologia* (Berl.) "Nicotine-Like . . . after . . . Mecamylamine in . . . rats," 46, pp. 119-121 (1976).

Rupniak, et al., "Antinociceptive and Toxic Effect . . . Attributable to Nicotinic Agonist Activity," *Brit. J. Pharmacol.*, 113(4): 1487-1493 (1994).

Sallee, F.R., et al., "Effects of pimozide on cognition in children with Tourette syndrome: interaction with comorbid attention deficit hyperactivity disorder," *Acta.1 Psychiatr. Scand.* , 90(1): 4-9 (1994).

Sallee, F.R.., et al., "Pharmacokinetics of pimozide in adults and children with Tourette's syndrome," *J. Clin. Pharacol.*, 27(10): 776-781 (1987).

Sallee, F.R., et al., "Relative efficacy of haloperidol and pimozide in children and adolescents with Tourette's disorder," *Am. J. Psychiatry*, 154(8): 1057-1062 (1997).

Sanberg, et al., "Nicotine as a Therapeutic Adjunct for Tourette's Syndrome," pp. 35-41 (1997).

Sanberg, et al., "Nicotine . . . with Tourette's Syndrome," *Biomed & Pharmacother.*, 43, pp. 19-23 (1989).

Sanberg, et al., "Nicontine . . . Striatal Mechanisms," *Pharmacol. Biochem & Behavior*, vol. 46: 303-307 (1993).

Sano Corporation website (1997).

Sawada, S., et al., "Augmenting action of nicotine on population spikes in the dentate gyrus of the guinea pig," *Neurosci Res.*, 20(4):317-322 (1994).

Schonenberger, et al.,"Preparation of Optically Active . . . ," *Helvetica Chimica Acta*, vol. 69, pp. 283-287 (1986).

Seumaru, et al., "Characteristics of tail-tremor induced by nivotine in rats," *Naonyn-Schmledeberg's Arch Pharmacol*, 350:153-157 (1994).

Shapiro, E., et al., "Controlled study of haloperidol, pimozide and placebo for the treatment of Gilles de la Tourette's syndrome," *Arch. Gen. Psychiatry*, 46(8): 722-730 (1989).

Shieh, et al., "Sexual Differences in the Diurnal Changes . . . of Neuron Activity in Rat: Role of Cholinergic Control," *Biology of Reproduction*, vol. 54, pp. 987-992 (1996).

Shytle et al., "Nicotine, Tobacco and Addiction," *Int'l Weekly Journal of Science*, vol. 384, pp. 18-19 (1997).

Shytle, et al., "Researchers Exploring . . . TS Treatment," *Tourette Syn. Assoc.*, 25(1): 1, 3, 7 (1997).

Shytle, et al., "Transdermal Nicotine for Tourette's Syndrome," *Drug Development Research*, vol. 38, pp. 290-298 (1996).

Silver, et al., "Case Study . . . In Tourette's Syndrome," *J. Amer. Child & Adolesc. Psych.*, vol. 35(12), pp. 1631-1636 (1996).

Stone, et al., "Chemistry and Structure-Activity Relationship of Mecamylamine and Derivatives," *Journal of Medicine & Pharm. Chemistry*, vol., 5(4), pp. 665-690 (1962).

*The Merk Index*, "5654. Mecamylamine," p. 905 (1989).

\* cited by examiner

MECAMYLAMINE

CHLORISONDAMINE

β-DIHYDROERYTHROIDINE

ERYSODINE

HEXAMETHONIUM

*FIG._1*

METHOD OF TREATING COGNITIVE DEFICITS IN LEARNING AND MEMORY

This application is a continuation-in-part of U.S. application Ser. No. 09/461,087, filed Dec. 14, 1999, and now abandoned, which is a continuation in part of U.S. application Ser. No. 09/198,882, filed Nov. 23, 1998, now U.S. Pat. No. 6,034,079, which is a continuation-in-part of Application No. PCT/US98/16634, filed on Aug. 11, 1998, now pending, which is a continuation-in-part of Application No. PCT/US97/20689, filed on Nov. 7, 1997, now pending, which is a continuation-in-part of U.S. Non-Provisional Application No. 08/935,364, filed on Sep. 22, 1997, now abandoned, which claims the benefit of U.S. Provisional Application No. 60/055,234, filed Aug. 11, 1997, now abandoned.

BACKGROUND

1. Field of the Invention

The present invention is in the field of pharmacotherapy of cognitive deficits in learning and memory by administering a nicotine antagonist alone, particularly mecamylamine. Examples of disorders associated with deficits in learning and memory are schizophrenia, bipolar disorder, obsessive compulsive disorder, attention deficit hyperactivity disorder, Alzheimer's Disease, and disorders of learning in children, adolescents and adults.

2. Background Information

Neuropsychological cognitive deficits in learning and memory are common in people with neuropsychiatric disorders (REF). For example, memory function is an important, but under-researched area for neuropsychological investigation in persons with bipolar disorder. Previous studies have reported cognitive deficits on tasks of declarative memory in bipolar patients in the euthymic state. Memory is more typically described as primary or immediate verbal memory and secondary verbal memory. Immediate memory is equivalent to short-term storage or information and is assessed with measures such as the Digit Span. This type of memory is not usually affected in amnesic patients. Secondary memory is memory for lists of words or stories, and it is often assessed after a time delay and is dysfunctional in amnesia. Card sorting refers to performance on the Wisconsin Card Sorting Test, which is considered a measure of executive functioning, concept formation, cognitive flexibility. Another aspect that is prominent in schizophrenia is the attentional deficit or lack of vigilance. Vigilance is often measured by a continuous performance test in which the subject is instructed to press a button in response to a specific target (a letter or number) but not other letters or numbers. This shows the ability to discriminate targets from nontargets (signal from noise).

Baddeley's model divides working memory into three components: a central executive that can manipulate information and two "slave" systems (one an articulatory loop for maintenance of verbal information and a visuospatial scratch pad for spatial information) (Baddeley A D. Science 255: 556–9, 1992). Verbal working memory refers to the integrity of the articulatory loop—the type of memory that is used to accurately retain a new telephone number long enough to make the call and that is essential for skill acquisition.

The changing scheme of drug reimbursement is forcing researchers to focus on the new drug's ability to help patients to function better in society. Previously successful treatment of schizophrenics was based on the abatement of the psychotic symptoms, such as hallucinations. The detrimental effects of schizophrenia on cognition have been recognized since the late 1800's. Emil Kraeplin originally coined the term "dementia praecox" occurring in a subset of patients with schizophrenia who experience, in addition to their chronic psychotic symptomatology, an ongoing dementing illness. The illness leads to progressive loss of IQ score, attention and memory loss. Recent studies with schizophrenic patients suggest that neuropsychological deficits in cognitive function contribute more to these patients' disability than do their symptoms of hallucinations and delusions.

Green (Am J Psychiatry 153(3): 321–330, 1996) reviewed many studies of schizophrenic rehabilitation and the correlation of rehabilitation with different symptoms, signs, and test results. He reviewed 1) studies that prospectively evaluated specific aspects of neurocognitive and community (e.g., social and vocational) functioning (six studies), 2) all known studies of neurocognitive correlates of social problem solving (five studies), and 3) all known studies of the neurocognitive correlates and predictors of psychosocial skill acquisition (six studies). Despite wide variation among studies in the selection of neurocognitive measures, some consistencies emerged. The most consistent finding was that verbal memory was associated with all types of functional outcome. Vigilance was related to social problem solving and skill acquisition. Card sorting (an indicator of executive function) predicted community functioning but not social problem solving. Negative symptoms (i.e., withdrawal) were associated with social problem solving but not skill acquisition. Notably, psychotic symptoms were not significantly associated with outcome measures in any of the studies reviewed.

Studies are beginning to focus on schizophrenia's effects on brain function and cognition. Recent clinical studies with newer atypical antipsychotics, such as risperidone, suggest that these drugs improve verbal working memory in schizophrenics; whereas, other drugs such as haloperidol do not (Green M F, Marshall B D, et al. Am J Psychiatry 154: 799–804, 1997). The authors posited that the beneficial effect of the newer antipsychotics was due to antagonistic action on the 5-hydroxytryptophan (5-HT2A) receptor. Conventional neuroleptics have primary affinity for the dopamine (D2) receptor and not 5-HT2A receptor.

Tourette's syndrome (TS) is an autosomal dominant neuropsychiatric disorder characterized by a range of symptoms, including multiple motor and phonic tics. Many TS patients also exhibit other neuropsychiatric abnormalities including obsessive compulsive symptoms (Pauls D L et al. Psychopharm Bull, 22: 730–733, 1986), hyperactivity and attention deficits (Comings D E, Himes J A, Comings B G, J Clin Psychiatry, 51: 463–469, 1990). Problems with extreme temper or aggressive behavior also are frequent (Riddle M A et al. WILEY SERIES IN CHILD AND ADOLESCENT MENTAL HEALTH, Eds. Cohen D J, Bruun, R D, Leckman J F, New York City, John Wiley and Sons, pp. 151–162, 1988; Stelf M E, Bornstein R A, Hammond L, A survey of Tourette syndrome patients and their families: the 1987 Ohio Tourette Survey, Cincinnati, Ohio Tourette Syndrome Association, 1988), as are learning disabilities (Harris D, Silver A A, Learning Disabilities, 6(1): 1–7, 1995; Silver A A, Hagin R A, DISORDERS OF LEARNING CHILDHOOD, New York City: Wiley, pp. 469–508, 1990).

Erenberg et al. (Erenberg G, Cruse R P, Rothner A D, Ann Neurol 22: 383–385, 1987) found that most patients with TS stopped neuroleptic medications by age 16, often because of side effects such as tardive dyskinesia. Many older, non-medicated TS patients are disqualified for full-time, responsible jobs.

It has been observed that 50% of children presenting with TS also have Attention Deficit Hyperactivity Disorder (ADHD). ADHD is a neurobiological disorder characterized by impaired attentiveness, increased impulsivity, and hyperactivity. ADHD is now the most commonly diagnosed childhood psychiatric condition, with some 3.5 million children afflicted. In addition, 60% of adolescents with ADHD continue to have symptoms in adulthood, representing another 2.5 million patients.

Added to the fourth edition Diagnostic and Statistical Manual of Mental Disorders was executive dysfunction, or an individual's inability to organize and effectively carry out nonroutine, goal-directed behaviors, and include problems in goal selection, planning, behavioral sequencing, judgment, working memory, and attention. This diagnosis cuts across traditional diagnostic boundaries. It occurs in both cortical and subcortical dementias, schizophrenia, affective disorders, traumatic brain injury and many other neuropsychiatric and neurological disorders. No one single test such as card sorting can adequately measure its impairment. However, executive dysfunction can be determined by a skillful history, functional impairments, and clinical observation. Attempts to treat executive dysfunction with medication have met with limited success (Mahurin R K, Sem in Clin Neuropsychiatry 4(1): 2–4, 1999).

Obsessive compulsive disorder (OCD) is associated with specific cognitive deficits on tasks of executive and visual memory function (Purcell R et al. Biol Psychiatry 43(5): 348–57, 1998). When Tourette's syndrome was combined with OCD or attention deficit symptoms, impaired achievement and execution functioning were correlated with obsessive and obsessive/attention symptoms, but not with attention symptoms alone (De Groot C M et al. J Neuropsychiatry Clin Neurosci 9(2): 267–72, 1997).

The current patent application is concerned with the administration of nicotine antagonists, particularly mecamylamine (3-methylamino-2,2,3-trimethylnorcamphane). Mecamylamine is well known as a nicotine antagonist and blocks ganglia which nicotine stimulates. First introduced as an anti-hypertensive, mecamylamine blocks sympathetic ganglia transmission and thereby causes vasodilatation and a fall in blood pressure (Taylor P, In: Goodman L S, Gilman A (eds) The Pharmacological Basis of Therapeutics, McMillan Publishing Co., New York City, pp. 193–95, 1996). Generalized ganglionic blockade may result also in atony of the bladder and gastrointestinal tract, impaired sexual function, cycloplegia, xerostomia, diminished perspiration and postural hypotension. While the clinical use of mecamylamine as a ganglionic agent has largely been replaced by more effective antihypertensive medications, scientists remain interested in mecamylamine because of its ability to block nicotine binding sites in the brain (see, e.g., Martin B R, Onaivi E S, Martin T J, Biochemical Pharmacology 38: 3391–3397, 1989; and Banerjee S et al, Biochemical Pharmacology 40(9): 2105–2110, 1990). These nicotine binding sites, known as nicotinic acetylcholinergic receptors (nAChr), are normally activated in the brain by acetylcholine, a prominent neurotransmitter. Mecamylamine's amnesic effects have been well documented (Rush D K, Streit K. Psychopharmacology (Berl) 106: 375–82, 1992; Elrod K, Buccafusco J J. J Pharmacol Exp Ther 258: 403–9, 1991).

Unlike some ganglionic blocking agents, which do not readily reach the central nervous system (CNS), mecamylamine has been reported to produce central effects in humans, such as blocking the CNS actions of nicotine (Martin B R, Onaivi E S, Martin T J, Biochemical Pharmacology 38: 3391–3397, 1989) and in altering cognitive functioning (Newhouse Pa. et al, Neuropsychopharmacology 10: 93–107, 1994), electrical brain waves (Pickworth W B, Heming R I, Henningfield J E, Pharmacology Biochemistry & Behavior 30: 149–153, 1988) and cortical blood flow (Gitalman D R, Prohovnik I, Neurobiology of Aging 13: 313–318, 1992).

In a recent study of the nicotine receptor (nicotine binding site) and its ion channel (mecamylamine binding site), Banerjee et al. disclosed that mecamylamine and several nicotine analogs have a high affinity for the mecamylamine site. Like mecamylamine, several nicotine analogs also have anti-nicotinic effects (Banerjee S et al. Biochem Pharmacol 40(9): 2105–10, 1990). Research is also proceeding on alkaloids which act on the nicotinic receptor channels (Daly J W: Alkaloids as Agonists, Antagonists and Noncompetitive Blockers of Nicotinic Receptor Channels. In: Proceedings of Nicotinic Acetylcholine Receptors as Pharmaceutical Targets. Jul. 24–25, 1997, Washington, D.C.).

Nicotine, via tobacco in various forms, has been one of the most widely utilized drugs for centuries (Wilbert J, J Ethnopharmacol 32(1–3): 179–186, 1991). Nicotine is a potent modulator of nAChrs (Changeux J P, Sci Amer (November) pp. 58–62, 1993). Through these receptors, nicotine activates the presynaptic release of several neurotransmitters including acetylcholine, norepinephrine, serotonin and dopamine (Balfour DJK, Pharmacological Therapeutics 16: 269–282, 1982). Agents which can modulate central monoaminergic neurotransmissions by acting on nAChrs may be useful therapeutically for treating neuropsychiatric disorders (Jarvick M E, Br J Addict 86: 571–575, 1991; Newhouse Pa., Hughes J R. Br J Addict 86: 521–526, 1991; and Hughes J, Clarke PBS (Eds): The effects of nicotine on biological systems II. Abstract S40, 1994; Decker MW et al, Life Sci 56: 545–570, 1995). Nicotine has been shown to improve cognitive performance (Wesnes K, Parrott A. SMOKING, NICOTINE AND HUMAN PERFORMANCE. HANDBOOK OF HUMAN PERFORMANCE. London, Academic Press, 1992. pp 127–67)

U.S. Pat. No. 5,774,052 to Rose and Levin discloses agonist-antagonist combinations to reduce the use of nicotine and other drugs. In combination with nicotine, the nicotinic antagonist mecamylamine was given to treat tobacco dependency. Rose and Levin proposed including both nicotine and mecamylamine in a patch. Rose and Levin also suggested that such agonist-antagonist combinations could be used in other psychopathological disorders and cases involving neuronal dysfunction (e.g., manic depression, schizophrenia and hypertension due to sympathetic autonomic disorder).

It would benefit patients to be able to have better symptom control and fewer side effects. In particular, it would be preferable to take a single drug to improve cognition and societal functioning, as did patients in at least some of the reports disclosed herein. Our clinical experience with mecamylamine in human patients with a variety of diagnoses supports use in improving cognition. Based on our experience with patients with Tourette's Syndrome, bipolar disorder, ADHD, and schizophrenia-like symptoms, persons with neuropsychological cognitive deficits in learning and memory are also likely to benefits from treatment with mecamylamine and other nicotine antagonists.

BRIEF SUMMARY OF THE INVENTION

It is an object of the present invention to provide new therapy for patients with impaired cognition, including impaired memory and cognition.

It is a further object of the present invention to provide therapy with fewer side effects to improve patient medication compliance, as well as to improve their quality of life and social functioning.

In one embodiment, there is disclosed a method of treating memory disorders in individuals in need thereof. The method includes administering to the individual an effective amount of a nicotine antagonist. Preferably, the effective amount of the nicotine antagonist is 0.005–10 mg/kg/day. Preferably the dose of mecamylamine is 0.005–1.0 mg/kg/day.

In another embodiment, there is disclosed a method of treating learning disorders in individuals in need thereof. This method includes administering to the individual an effective amount of a nicotine antagonist. Preferably, the effective amount of the nicotine antagonist is 0.005–10 mg/kg/day. Preferably the dose of mecamylamine is 0.005–1.0 mg/kg/day.

In another embodiment, there is disclosed a method of treating age-related cognitive disorders in an individual in need thereof. The method includes administering to the individual an effective amount of a nicotine antagonist. Preferably, the effective amount of the nicotine antagonist is 0.005–10 mg/kg/day. Preferably the dose of mecamylamine is 0.005–1.0 mg/kg/day.

Preferably, mecamylamine, a stereoisomer, or a mecamylamine analog is used. The effective amount of mecamylamine is that which improves the individual's memory function.

In another embodiment, there is disclosed a method of treating cognitive disorders in an individual in need thereof. The method includes administering to the individual an effective amount of partial nicotine agonist.

DETAILED DESCRIPTION OF THE INVENTION

Figure 1:
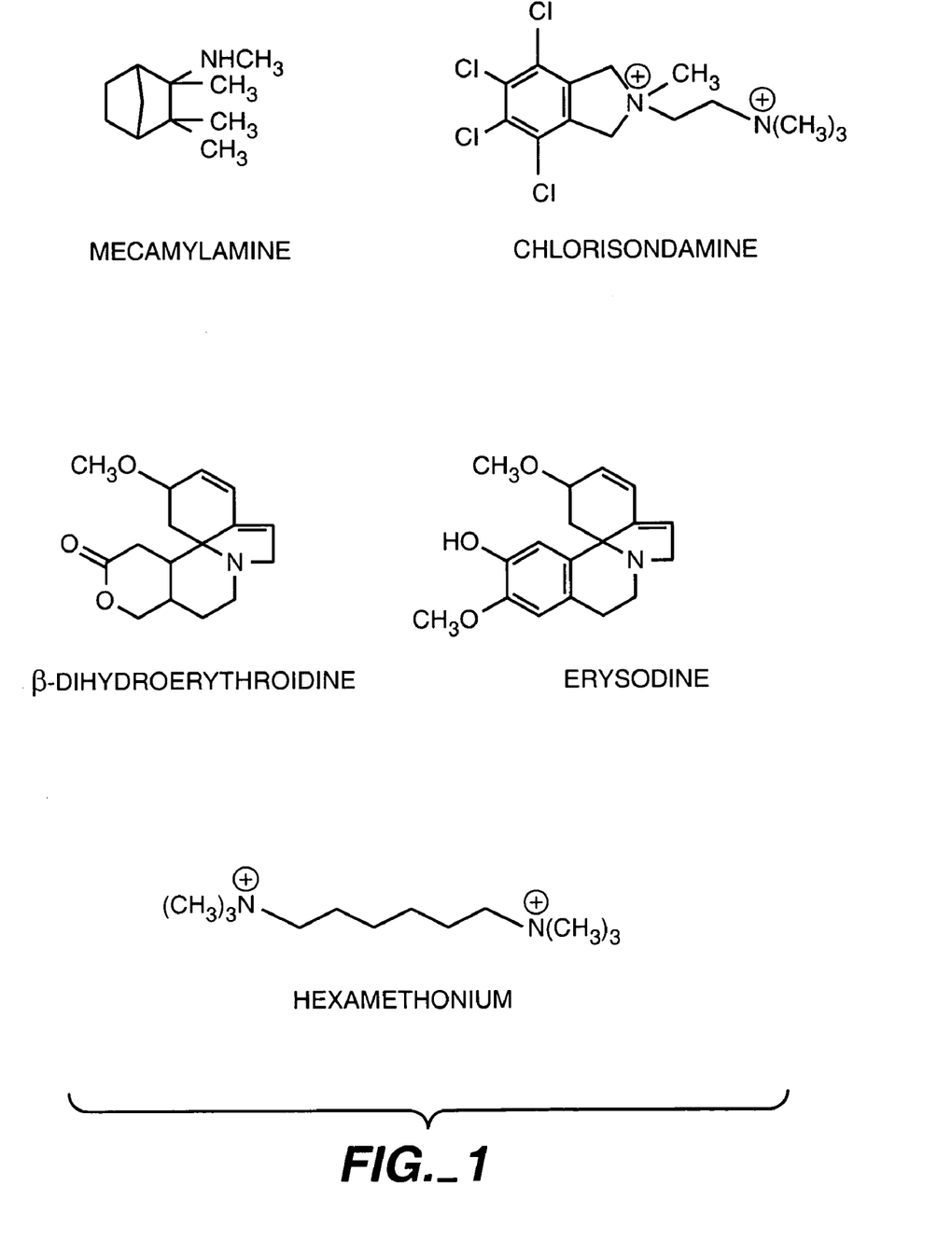
FIG. 1 shows the chemical structures of mecamylamine and several other nicotinic antagonists.

In a few TS patients whose symptoms and cognitive deficits were not responding to the usual treatments, we found that mecamylamine, the nicotine receptor antagonist approved for the treatment of hypertension, also relieved the cognitive deficits. The improvement in cognitive deficits following mecamylamine treatment alone or in combination with neuroleptics was unexpected, since one would generally expect the effects of mecamylamine to oppose those of nicotine, which is known to improve memory. Thus, the significant improvement seen in patients with mecamylamine treatment is a surprising development. We believe that in addition to mecamylamine, other nicotine receptor antagonists, discussed in detail below, also could be used. Furthermore, based on effects on co-existing illnesses, we believe that nicotine receptor antagonists are useful not only in TS, but also in such other neuropsychiatric disorders such as attention deficit hyperactivity disorder (ADHD), Obsessive Compulsive Disorder (OCD), Essential Tremor (ET), Tardive Dyskinesia (TD), Depression (D), Huntington's Disease (HD) and Alzheimer's Disease (AD). Nicotine antagonists can also be expected to improve cognition in other nicotine-responsive disorders (e.g., schizophrenia, depression, bipolar disorder, and stress and panic states). Furthermore, the administration of a nicotine antagonist in combination with either conventional or atypical neuroleptics helps cognition, which in turn contributes to the schizophrenic's ability to function in society.

We believe that these effects of mecamylamine are due to a previously unrecognized partial agonist activity of mecamylamine at low doses. The doses used in this study are far below those used to treat hypertension, in which the goal was nicotinic inhibition across a wide variety of receptors. For some hypertensive patients, too many receptors were inhibited, resulting in unwanted side effects in diverse body functions (see above). We believe that the partial agonist effect has been demonstrated in the patients presented below who received doses in the range of 0.03 to 0.1 mg/kg/day. To the extent that this agonist activity is shared by other "nicotinic antagonists," those nicotinic antagonists are also included in this invention.

In a recent study, bipolar patients performed worse than control subjects on measures of declarative memory but did not differ from the performance of control subjects on either of the two procedural learning tasks. These results suggest disturbed function of temporal lobe, but not basal ganglia, structures in persons with bipolar disorder (Van Gorp et al. Biol Psychiatry 46: 525–31, 1999). In addition, there has been more recent data that patients with bipolar disorder suffer from continuing specific cognitive deficits even when in apparent "clinical remission." Of particular note are problems in "declarative memory" which involves the temporal lobes and hippocampus. This deficit in declarative memory appears to dramatically decrease the ability of patients with bipolar disorder to recover fully and function normally.

Executive function deficits have been reported in children with ADHD, including tests of spatial short-term memory, spatial working memory, set-shifting ability, planning ability, spatial recognition memory, and delayed matching to sample, while pattern recognition memory was normal. ADHD children medicated with stimulants had normal functions in the preceding tests, except for deficit in spatial recognition memory (Kempton s et al. Psychol Med 29(3): 527–38, 1999).

Recently, mecamylamine was tested for its effect on executive function in rats and aged monkeys. Mecamylamine in several doses was administered IP to rats tested in the Morris Water Maze (MWM) (0.33 and 1.0 mg/kg), to rats trained to perform a delayed stimulus discrimination task (DSDT) (0.01, 0.025, 0.05, 0.1, 0.25 and 5 mg/kg), and IM to aged rhesus monkeys (average 24.6 yr) trained to perform a delayed matching to sample task (DMTS) (0.01, 0.025, 0.05, 0.1, and 0.25 mg/kg). In rats, 1.0 mg/kg of mecamylamine significantly improved location of the hidden platform on day 1 of MWM but inhibited learning in subsequent trials; no significant effect was observed with 0.33 mg/kg. Rat DSDT accuracy increased significantly with four doses of mecamylamine (0.1, 0.025, 0.1 and 0.25 mg/kg). Mecamylamine doses of 0.25 and 0.5 mg/kg doses improved accuracy at 10 min in aged monkeys in DMTS and doses of 0.05, 0.1 and 0.25 mg/kg had significant decreases at 24 hr after administration (Terry A A, Buccafusco J J, Prendergast M A. Drug Dev Res 47: 127–36, 1999).

Age-related memory disorder, or benign senescent forgetfulness, is a general classification for elderly who have more memory impairment than their age peers, but less than demented elderly. There has been debate as to whether the changes in brain function found in normal aging, benign senescent forgetfulness and Alzheimer's disease are fundamentally different or are part of a continuum (Brayne C and Calloway P. Lancet Jun. 4, 1988, pp 1265–1266). Age-related cognitive impairment in healthy individuals may include less efficient acquisition of new information; diminished retention of information; reduced ability to plan new activities, solve problems and make complex decisions; and often reduced attention (Jolles J et al. Drugs & Aging 7(6): 459–479, 1995[The MAAS study]). In other words, age-related cognitive impairment includes some or all aspects of executive dysfunction.

Most patients who survive carbon monoxide poisoning have cognitive impairments, including impaired vigilance, executive dysfunction and slower mental processing (Gale S D et al. Brain Injury 13(4): 229–43. Patients with mild traumatic brain injury (RBI) have neurologic deficits that are best diagnosed through the use of tests that measure executive and frontal-lobe functioning (Brooks J et al. J Trauma 46(1): 159–63, 1999). Chronic exposure to organic solvents has been associated with a higher rate of neuropsychological abnormality, including vigilance, memory, and functional disorders (Jang J-Y et al. Int Arch Occup Environ Health 72: 107–14, 1999). These individuals also could benefit from treatment with a selective nicotine agonist, such as mecamylamine.

Definitions

"Nicotine Antagonists", of which mecamylamine is but one example are a large and growing category. A truly exhaustive list of such compounds would take up too much space here. The following discussion is not intended to be exhaustive but to teach how to identify compounds which are encompassed by this term. Currently interesting nicotinic antagonists and related compounds in research were discussed by Daly J W (ibid) which is incorporated by reference. Clark and Reuben (Br. J. Pharmacol. 117: 595–606, 1996) disclose dihydro-beta-erythroidine, methyllycaconitine, chlorisondamine, and trimetaphan. Normecamylamine, N-(1,2,2)trimethyl-1-bicyclo[2,2,1,] -heptyl-benzenamine, dimethylaminoisocamphane, exo-aminonorbornane, 2,2,6,6-tetramethylpiperdine, 2,2,6,6-tetramethyl-4-aminopiperdine, and pempidine were identified as active nicotinic antagonists (Banerjee et al., Biochemical Pharmacology 40: 2105–2110, 1990). This article and its test methods are hereby incorporated by reference. Additional examples of nicotine antagonists include erysodine (Decker, European Journal of Pharmacology 280: 79–89, 1995), phenyltropane carboxylic acid methyl esters (Lemer-Marmarosh et al., Life Sciences 56(3): PL 67–70, 1995), arylpempidine analogues (Wang et al., Life Sciences 60(15): 1271–1277, 1997); ibogaine (Daly, Biochemical Pharmacology 40(9): 2105–10, 1990).

In addition, the various stereoisomers and substituted analogs of mecamylamine have been tested for activity (Stone et al., J Med Pharm Chem 5(4): 665–90, 1962, hereby incorporated by reference). Activity, as tested in rats by nicotine convulsions and pupil dilatation, was routinely lost with larger substitutions for the methyl groups. Both methyl or dimethyl groups on the amino group were more active than other substituents. The d form was active; however, the dl racemate appeared to be slightly more active. Consequently, we are postulating that the l form has significant activity in this use of mecamylamine. Stone et al. reported that the exo form (methylamino group lies on the same plane as the methylene bridge) was always stronger than the endo form (methylamino group lies below the methylene bridge and tends to lie within the cage created by the bridge). In addition, a partial structure, 2,2,-dimethyl-3-methylaminobutane, also was active. Slight differences in activity between different models for the d form and other analogs indicate that there may be differential activity and effectiveness in neuropsychiatric disorders.

Other compounds which may reasonably be expected to be active in this use are disclosed in U.S. Pat. No. 4,837,218 (Alkylated Bicycloalkaneamines for Neurotoxic Injury), U.S. Pat. No. 2,894,987 (N-allyl-2-aminoisocamphane), U.S. Pat. No. 3,148,118 (Analeptically Active Agents), U.S. Pat. No. 3,164,601 (Analeptically Active N-Substituted Aminonorcamphane Derivatives). These patents are incorporated by reference. Compounds can be initially tested in rat and primate models disclosed above, including but not limited to the Morris Water Maze, delayed stimulus discrimination test, and delayed matching to sample task.

"Beneficial effect" is an observable improvement over the baseline clinically observable signs and symptoms. For example, a beneficial effect in cognitive disorders can be determined by a history of improved job performance; better organization; improved goal selection, planning and attainment. A beneficial effect in cognitive disorders can also be determined from various standardized tests, such as the Cambridge Neuropsychological Test Automated Battery (CANTAB), which is sensitive to executive function deficits and can report a variety of cognitive impairments, including spatial short-term memory, spatial working memory, set-shifting ability, planning ability, spatial recognition memory, delayed matching to sample, and pattern recognition memory.

"Neuroleptic drug" as used herein is a drug which is used primarily to treat psychosis. Such drugs also affect thinking, feeling and neurological status, particularly movement and posture (as in TS). Almost all neuroleptic drugs have a strong extrapyramidal effect, resulting in tardive dyskinesia (see above). Examples of conventional neuroleptic drugs are haloperidol (Haldol®, McNeil Pharmaceutical, Raritan, N.J.), pimozide (Orap®, Teva Pharmaceuticals, Kulpsville, Pa.), fluphenazine, sulpiride (Synthelabo, Paris) and raclopride (Astra, Sweden). These have a reputation for reducing cognitive function, even when psychotic symptoms improve (Borison Acta Psychiatr Scand Suppl 389: 5–11, 1996). New atypical neuroleptics include but are not limited to risperidone (Risperdal®, Janssen Pharmaceutical, Titusville, N.J.), clozapine (Clozaril®, Novartis, Summit, N.J.), thioridazine (thioridazine hydrochloride, Mylan, Morgantown, Wva), iloperidone (Hoechst-Roussel, Somerville, N.J.), olanzapine (Zyprexa®, Lilly, Indianapolis, Ind.), quetiapine (Seroquel®, AstraZeneca, Wilmington, Del.), sertindole (Abbott, Abbott Park, Ill.), and ziprasidone (Zeldox®, Pfizer, New York City). These have been found to improve cognition, possibly by stimulation of histamine neuron activity via blockade of the 5-HT2A receptor.

The term "effective amount" refers to the amount of nicotine antagonist or partial nicotine agonist that is necessary to provide benefit. The precise amount required will vary depending upon the particular compound selected, the age and weight of the subject, severity of the disorder, route of administration, and so forth, but may easily be determined by routine experimentation, as described below in the clinical examples. In general, however, an effective amount will range from about 0.001 mg/kg to about 10 mg/kg per day, preferably about 0.002 mg/kg to about 7 mg/kg, more preferably about 0.005 mg/kg to about 2 mg/kg, and most preferably about 0.01 to about 1.5 mg/kg. Doses of mecamylamine can range from about 0.005 to 1.0 mg/kg/day and more preferably about 0.01 to 0.5 mg/kg/day. A starting dose is about 2.5 mg per day, with dosage adjusted according to abatement of symptoms (see case histories below). A small child preferably starts with 1 mg per day or less; however, a small child may require a higher mg/kg dose.

The term "pharmaceutically acceptable" refers to a lack of unacceptable toxicity in a compound, such as a salt or excipient. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, citrate, and the like. Pharmaceutically acceptable excipients are described at length by E. W. Martin, in Remington's Pharmaceutical Sciences (Mack Publishing Co.).

Pharmaceutical compositions containing nicotine antagonists may contain one or more pharmaceutical carriers. The term "pharmaceutically acceptable carrier" refers to any generally acceptable excipient that is relatively inert, non-toxic and non-irritating. When the carrier serves as a diluent, it may be solid, semisolid, or liquid material acting as a vehicle, excipient, or medium for the active ingredient. Pharmaceutical unit dosage forms may be prepared for administration by any of several routes, including, but not limited to, oral and parenteral (especially by intramuscular and intravenous injection, or by subcutaneous implant or transdermal administration). Representative of such forms are tablets, soft and hard gelatin capsules, powders, lozenges, chewing gums, emulsions, suspensions, syrups, solutions, sterile injectable solutions, and sterile packaged powders. Compositions containing nicotine antagonists may be formulated by procedures known in the art so as to provide rapid, sustained, or delayed release of any or all of the compounds after administration.

As the nicotine antagonist formulation of the present invention is well suited to oral administration, preferred carriers facilitate formulation in tablet or capsule form. Solid pharmaceutical excipients such as magnesium stearate, calcium carbonate, silica, starch, sucrose, dextrose, polyethylene glycol (PEG), talc, and the like may be used with other conventional pharmaceutical adjuvants including fillers, lubricants, wetting agents, preserving agents, disintegrating agents, flavoring agents, and binders such as gelatin, gum arabic, cellulose, methylcellulose, and the like, to form admixtures which may be used as such or may be tabulated, encapsulated, or prepared in other suitable forms as noted above. A general description of formulation is given in Remington's Pharmaceutical Sciences (Mack Publishing Co.).

Administration

Administration is preferably by oral dosage but may be by transdermal application, intranasal spray, bronchial inhalation, suppository, parenteral injection (e.g., intramuscular or intravenous injection), and the like. Carriers for parenteral administration include, without limitation, aqueous solutions of dextrose, mannitol, mannose, sorbitol, saline, pure water, ethanol, glycerol, propylene glycol, peanut oil, sesame oil, polyoxyethylene-polyoxypropylene block polymers, and the like. One may additionally include suitable preservatives, stabilizers, antioxidants, antimicrobials and buffering agents, for example, BHA, BHT, citric acid, ascorbic acid, tetracycline, and the like. Alternatively, one may incorporate or encapsulate the nicotine antagonist formulation in a suitable polymer matrix or membrane, thus providing a sustained-release delivery device suitable for implantation or application to the skin. Other devices include indwelling catheters and devices such as the Alzet® minipump.

The invention has been disclosed by direct description. The following are examples showing the efficacy of the method in providing benefit. The examples are only examples and should not be taken in any way as limiting to the scope of the method.

EXAMPLES

Clinical Examples

Patient 1 was a tall, 173-pound, 15-year-old male diagnosed with TS. He had been a patient in our clinic, receiving 2 mg of haloperidol daily and two transdermal nicotine patches (14 mg/24 hr) each week for approximately one year for effective control of severe symptoms of TS. However, approximately two months before a scheduled follow-up visit, his tics, which had been controlled, had emerged again. At that time, his haloperidol dose was increased to 3 mg/day and the frequency of nicotine patch application was increased to every other day, with some improvement noted. However, the side effects of the nicotine patch, particularly nausea, were disturbing to the patient, resulting in his refusal to wear the patch. In addition, because of the increased risk of nicotine addiction with daily use, we were reluctant to subject the patient to continued use of the patch.

Two weeks before his visit to our clinic, the nicotine patch was discontinued. Eye-blinking, eyebrow raising, facial grimacing, head jerks, abdominal tics, and leg/foot movements were present. His score on the YGTSS was 17/30; his tics totaled 245 over a 5-minute period with overall severity rated as 3 (moderate) on a 7-point scale.

Mecamylamine (5 mg) was given orally at about 11:30 AM. Approximately two hours later, the patient reported that his urge to tic was reduced. The YGTSS score was 6/20. Although tics were still present, there was a decrease in tic frequency and in tic severity. By 6:00 PM, his mother reported that the patient felt better, there were virtually no tics present, and there were no side effects. However, by the next morning, his tics were beginning to return. One month later, on a daily dose of 5 mg mecamylamine at breakfast, his tics were still under control, and the patient reported that he was more relaxed and alert. The shy, taciturn youth of 30 days earlier was now more outgoing and voluble.

The clinical experience of treating this first patient suggested that, in combination with haloperidol, mecamylamine could be used to suppress motor tics. The effect of mecamylamine after a single oral dose was seen in 2–3 hours and lasted approximately 8–12 hours.

Patient 2 was a 16-year-old in the ninth grade whose overall cognitive functioning was in the high-average range but he had a severe deficit in visual-motor function. He developed motor and vocal tics at 10 years of age, within six months after starting on methylphenidate and Dexedrine (dextroamphetamine sulfate, SmithKline Beecham Pharmaceuticals, Philadelphia, Pa.) for attention deficit disorder and academic difficulty. With 0.1 mg of clonidine three times a day, his tics were said by his parents to be under control. However, for the past two years, he had taken no medication for motor and vocal tics. By the end of eighth grade, he had failed math, received C and D grades in his other subjects and had marked difficulty with any visual-motor function. His handwriting was slow and labored; he resisted any written work, became frustrated with it, and felt that he was doomed to failure. On his visit to our clinic, his tics were clearly evident: eye blinking, mouth grimacing, gross body tics, quick and jerky movements of his shoulders, head tics, and sniffing. He complained that he was "active in his head" (distractible). During the summer he was attempting to learn math so that he could retake the examination and enter high school in the fall. However, he was having difficulty writing down the steps needed to answer the math problems (as is required in the examination) although he can "get the steps in his head." He was impatient, frustrated and giving up.

Mecamylamine was prescribed and the patient was told to take it after dinner. His mother, a nurse, reported that two hours after taking 5 mg of mecamylamine he started to study his math. He felt his "mind is clearer", was more relaxed, and worked on math problems for three hours without distraction. His tics had subsided in intensity and frequency. The following morning, he felt restless; and tics started to return, though not as disturbing as previously. He had eye blinking and gross, jerky body movements. He was prescribed 5 mg of mecamylamine at breakfast and 2.5 mg after dinner daily. Twelve days later, the patient reported that with the medication, he was not "hyper" and could concentrate on his schoolwork. The tics, although occasionally present, had subsided. His blood pressure was unchanged at 114/80. In this patient, no neuroleptic drugs were given in combination with mecamylamine, which suggests that mecamylamine alone can suppress TS symptoms. After eight weeks of treatment, the patient's mother reported that he was doing fine and wanted to continue therapy and had entered high school.

Patient 3 was a 35-year-old, who has had TS with severe motor and vocal tics, obsessions and compulsions since the age of six. She is the mother of three children, the oldest of whom, a girl aged 12, also has TS. Over several years, a variety of medications had been tried, including Zoloft (sertraline hydrochloride, Roerig Div, Pfizer, New York City) to limit her depression and mood swings. In June 1996, with a trial of the transdermal nicotine patch (7 mg) given in our clinic, her tics subsided within three hours. However, in the next 24 hours, knee, ankle and wrist joints became painful and swollen; and the patch was discontinued. A trial dose of haloperidol (0.5 mg) was then given. In 12 hours, she experienced a precipitous rise in temperature that necessitated discontinuation of haloperidol. On follow-up at our clinic one year later, she was tense and unhappy and displayed multiple and severe tics, almost continual eye blinking, grimacing, nose twitching, sniffing, and a compulsive need for everything to be "just right" in her home.

She was started on 5 mg of mecamylamine at 2 PM. At 5 PM there was a distinct obtundation of tics which, although still present, were markedly reduced (50%) in intensity. She was continued on 5 mg mecamylamine for 4 days and reported that the tics were still present but less intense. She reported feeling relaxed with decreased anxiety. Moreover, she reported that her urges to have rage outbursts during stressful situations were reduced while taking mecamylamine. The daily dose of mecamylamine was continued for 30 days with no appreciable change in blood pressure or heart rate. She complained of constipation during her menses, but reported no other side effects. She requested that the mecamylamine be continued. In this patient, as with patient 2, a neuroleptic was not necessary. She had been on mecamylamine for 195 days, and then in a check-up call, she said she had discontinued taking the mecamylamine because although she appreciated her moods being less volatile, she missed her "highs."

Patient 4 was a 43-year-old salesman with a history of TS since age 14. He had received haloperidol (0.5 mg bid) and a 14 mg transdermal nicotine patch twice each week for the previous 6 months, without complete control of motor or vocal tics. Rather than increase the haloperidol dose or increase the frequency of nicotine patch, the nicotine patch was discontinued and mecamylamine (5 mg per day) was prescribed. At baseline, the YGTSS was 27/30, and a 5-minute segment of videotape revealed a total tic count of 207 with an overall severity of 4 (very noticeable) on a 7-point scale. Approximately 90 minutes after the first dose of mecamylamine, the patient reported that he felt more relaxed; his YGTSS score was 20/20; and severity was 2.5 (slightly noticeable). Six hours later, the patient reported that his feeling of relaxation persisted, and the facial grimacing and head jerks were not apparent. His eye blinking, although still occurring, was decreased in severity. However, by the next morning, the tics were beginning to return. With 5 mg of mecamylamine at breakfast, obtundation of tics within 1–2 hours was again apparent. Approximately eight hours later the tics began to return. An additional dose of 2.5 mg of mecamylamine before dinner was prescribed. This dose controlled motor and vocal tics during the evening. A maintenance dose of 5 mg mecamylamine with breakfast and 2.5 mg before dinner was prescribed. Haloperidol (0.5 mg bid) was continued. Nicotine was discontinued. The combined use of mecamylamine and haloperidol, each in small doses, controlled motor and vocal tics.

Recently patient 4 reported that his primary care physician could not find a cause for his chronic fatigue that had started before mecamylamine treatment. There was no change in blood pressure. However, the patient discontinued mecamylamine.

Patient 5 was an 18-year-old male who was first seen in our clinic at age 15. His TS symptoms had been treated with pimozide (Orap, Teva Pharmaceuticals, Kulpsville, Pa.) up to 16 mg daily since age 10. He had a strong family history of tic spectrum disorders. His mother, maternal grandfather, maternal uncle and a male cousin all had evidence of Tourette symptoms. At his initial clinic visit, he was receiving 12 mg of pimozide together with Prozac® (fluoxetine hydrochloride, Eli Lilly & Co., Indianapolis Ind.). His motor tics were minimal but he was depressed with severe Parkinsonian-like facies and a fine motor tremor of his hands aggravated by intention. Decreasing pimozide to 4 mg daily and discontinuing Prozac resulted in relief of both depression and Parkinsonian-like symptoms, except for the persistent hand tremor. During the course of his treatment with us, an abnormal EEG with mild background disorganization and sharp activity lateralized to the left temporal region was found. He was treated with carbamazepine, haloperidol and Cogentin® (benztropine mesylate, Merck & Co., West Point, Pa.) with marked reduction in motor and vocal tics. However, the tremors persisted, and obsessive and compulsive symptoms became prominent. He said he could not focus on a task because his mind was "wandering to something else". A trial of nicotine patch resulted in nausea, headache and noncompliance. Two months later on a visit to the clinic, a trial of mecamylamine 2.5 mg was given. Within two hours, this patient said, "I feel really calm", and he said feeling like this, he could go back to his community college studies. In addition, the hand tremor, so pronounced before mecamylamine administration, had almost disappeared. However, after approximately one month, this patient discontinued mecamylamine, saying that he no longer needed it. He continued a low dose of haloperidol and a low dose of fluoxatine.

Patient 6 was a 23-year-old male, who had had severe Tourette symptoms since he was in second grade. Over the years he had been treated with a variety of neuroleptic medications as well as clonidine and clonazepam (Klonopin®, Roche Laboratories, Nutley, N.J.) At his first visit to our clinic, he had been receiving 12 mg of pimozide daily for at least two years, and was working as a counselor at a camp for emotionally disturbed children. Twice he had failed his courses to become an Emergency Medical Technician. His Tourette symptoms were among the most severe seen at our clinic. He was in constant restless motion, his speech was under pressure, there were tic-like grimaces on his face, shrugging of his shoulders, copropraxia (his fingers darting to his groin), but most prominent was coprolalia. Every other word was punctuated with an expletive, sexual in nature, under pressure, distinct, and loud. He tried to cover up using a smile and joviality. However, he was frightened and depressed and had a significant tremor of his fingers. On neuropsychological testing, severe visual-motor problems were evident. A trial of 7 mg of transdermal nicotine resulted in a mild decrease in intensity of his tics and coprolalia. However, within 4 hours he became nauseous and dizzy. Nicotine patch was tried daily for one week increasing the time it was applied. However, side effects continued, and nicotine was discontinued.

After a 2-week washout of nicotine, 2.5 mg of mecamylamine daily was prescribed. At the end of 7 days, the patient reported that about 70% of his coprolalia had subsided. Follow-up at that time confirmed not only the significant decrease in coprolalia, but now what remained was whispered. His restlessness too subsided, as did the facial grimaces. Only a trace of hand tremor remained.

Patient 7, a 16-year-old female high school student, was first seen in our clinic in July 1997, has a long history of Tourette's Syndrome, obsessive-compulsive disorder and depression for which she has been receiving Klonopin 1 mg tid with minimal improvement in tics. With the addition of sertraline 25 mg bid and transdermal nicotine patch there was a noticeable improvement in tics and in mood. However, the side effects of the nicotine patch including headaches and nausea prompted discontinuing the nicotine patch. In mid-August 1997, mecamylamine 2.5 mg was prescribed, sertraline gradually discontinued and Klonopin reduced to 1 mg/day. Within 2 to 3 days, she reported tics "remarkably diminished" and mood improved with decreased irritability. In early December 1997, however, her mother reported "aggression and self doubt" had started again, and a sniffing vocal tic returned. Increasing mecamylamine to 3.75 mg daily was accompanied by relief of depression, moodiness and irritability, moderate improvement of tics (+4 to +5 on a scale of 10), and improvement in attitude to school and friends. Patient continued mecamylamine for 546 days. There have been no complaints of mecamylamine side effects.

Patient 8, a small, wiry 9 year old, had been diagnosed as having ADHD at 5 years of age and had received methylphenidate (20 mg bid) for approximately 6 months before being seen in our clinic. Although methylphenidate did help with attention, he developed motor tics within 4 months of its use. Methylphenidate was then discontinued and he proved to be intolerant to a 7-mg transdermal nicotine patch because of nausea. Mecamylamine 2.5 mg was only minimally effective; 3.75 mg daily, however, reduced his hyperactivity and helped him sustain attention. He said he felt better, and the "demon's voice" he no longer heard. On the global improvement scale, his mother rated him as a +3 on a scale of 10. There have been no reported side effects in 210 days.

Patient 9 had been seen in our clinic when he was 11 years of age. His oppositional behavior was such that his mother sent him to live with his a paternal uncle in another state. Seen in our clinic again at age 14, his motor and vocal tics were still severe; but he was now willing to consider treatment. Risperidone (2 mg/day) and transdermal nicotine patch 7 mg/day (approximately 2 patches per week) relieved his symptoms. However, he was still moody, irritable, and demanding. Mecamylamine 2.5 mg daily was added. Within 3 weeks his mother reported that since mecamylamine was added he has "the best improvement he has ever made", he is much calmer, his eye blinking tic has subsided, and outbursts of rage have decreased. During telephone follow up 6 months after mecamylamine was started, his grandmother reported that patient 9 had discontinued risperidone on his own initiative. And on his own initiative too, he had discontinued mecamylamine after about 5 months of therapy. He continued to use a nicotine patch with a frequency of "usually more than one each week". She reported that his tics were mostly under control; however, he is demanding and has occasional rages.

Patient 10 was a 37-year-old alcoholic smoker, who was depressed, had severe and incapacitating coprolalia and anxiety attacks, had been treated with antidepressants, benzodiazepines, and with haloperidol with limited relief of symptoms. Compliance in use of medications, however, was inconsistent. Mecamylamine, 2.5 mg daily was started on Jul. 1, 1997. The patient reported that he was "more relaxed, speaks better [coprolalia diminished], and speech more fluent". However, he complained of "headaches and heartburn". Mecamylamine was tried again on Dec. 8, 1997. On initial dose of 2.5 mg, coprolalia was under control for about 1 hour, following which the patient complained of "getting jittery and nervous". Mecamylamine was discontinued.

Patient 11 was a 14-year-old boy with Tourette's Syndrome, ADHD, OCD, severe visual-motor dysfunction, anxiety, and low self esteem. An avulsion of his thumb contributed to his feeling of being "incomplete" and physically different from his classmates. His symptoms were under moderate control with haloperidol. Transdermal nicotine potentiated the therapeutic effect of haloperidol, but he never was comfortable with the patch and finally rejected nicotine because of nausea. On Jul. 17, 1997, mecamylamine at 2.5 mg per day was started. Within 3 hours of the first dose the patient was less restless and felt calm. His tics had markedly decreased in severity. There were no adverse effects and blood pressure remained at 110–114/70–76. Within the week after mecamylamine was started, his mother reported a marked improvement in mood and behavior, decreased irritability and pleasant interactions with parents. "He does not hit his little brother any more." Haloperidol and clonidine, which had been continued, were decreased in dose. Mecamylamine was continued for 215 days. During this time, he had "excellent improvement" in terms of mood, behavior and attitude toward school. However, he had a persistent cough that did not remit. In an attempt to relieve the cough, mecamylamine was discontinued and sertraline started. The troublesome cough then occurred only at meal times. Return to mecamylamine was under consideration.

Patient 12 was started on methylphenidate for distractibility and hyperactivity when he was 9. Tics began within months of starting methylphenidate. The symptoms of Tourette's syndrome, OCD, and ADHD had become progressively worse. He had received a combination of medication including pimozide, haloperidol, Prozac, and Paxil, together which caused mild control of his tics, increased depression and sleeping in school, so much so that he was removed from his current grade (8th) at school and was home-schooled for 2 months before he was brought to our clinic at age 14.5 years. Gradually decreasing his various medications to haloperidol 2 mg and adding clonidine did not significantly alter his symptoms. Transdermal nicotine patch (7 mg) twice weekly did obtund his symptoms. However, when nicotine was discontinued and mecamylamine 3.75 mg/day was added, there was definite improvement in motor and vocal tics. Although still present, the tics are markedly obtunded and of low intensity. His mood is relaxed. He is doing well in school and is participating in high school athletic programs. Immaturity in the Bender-Gestalt test is no longer present. His blood pressure on December 1997 was 114/80; on Jun. 12, 1998, 100/70. There were no complaints.

Patient 13 was a 12-year-old boy had been seen in our clinic since he was 9 years of age. Motor and vocal tics, and compulsions have become increasingly worse after the age of 4 years, more so after 7 years. Repeat EEG's were abnormal "dysrhythmia grade III, bilateral synchronous and independent central, parietal temporal spikes". Tegretol aggravated all symptoms. His motor and vocal tics have been difficult to control with standard medication; he was sensitive to nicotine which, although helping obtund his tics, caused intolerable side effects. On Aug. 13, 1997, mecamylamine, 2.5 mg/day, was started. The patient reported that "I was calmed down, not grunting so hard." However, his improvement lasted only 3 to 5 days when tics started up again, and headaches became severe. Increasing the dose to 5 mg/day did not decrease tics but did increase headaches. Blood pressure which usually was between 110/76, went down to 90/68; pulse rate usually between 70 and 76, was 68. Mecamylamine was discontinued.

Patient 14 was an unusual 9-year-old boy, dysplastic in appearance, physically small, triangular shaped head, in constant movement, and chattering about his obsessions of guns and weapons. He had severe motor and vocal tics, coprolalia, compulsive touching, marked anxiety. He had received various medications including carbamazepine, methylphenidate, both of which only increased activity. Haloperidol reduced his activity but its effect lasted only about 3 weeks. A transdermal nicotine patch (7 mg) only made him nauseous. Mecamylamine on a 1.25 mg dose per day also appeared to increase his restlessness and make him weepy and irritable. It was discontinued after 10 days.

Summary of Clinical Findings: There were no specific tests of executive function, vigilance or various other memory components which are essential for learning. However, the clinical reports indicate improved learning: a) improvement in school (patient 11), b) doing well in school (patient 12), c) mind is clearer and could concentrate on homework (patient 2), d) could return to college (patient 5), and e) improved attention span and no voices (patient 8). In addition, patients 3 and 7 had compulsive behavior, which decreased with mecamylamine treatment. At the doses administered, there was one patient with significant blood pressure changes. Because mecamylamine at higher doses is approved for hypertension, the lower doses should be and were well tolerated. In this group of patients treated with mecamylamine, there was a reduction in symptoms of inattention, hyperactivity, obsessive compulsive behavior, depression and mood swings.

Dosages for patients are summarized below in Table 1. Dosages ranged from about 0.03 to 0.10 mg/kg. This range was used to calculate Table 2.

TABLE 1

Tested Therapeutic Doses of Mecamylamine (Inversine ®)

| Sex | Diagnosis | Age | Daily Dose (mg) | Weight (lbs) | (kg) | mg/kg |
|---|---|---|---|---|---|---|
| M | TS | 15 | 5 | 173 | 78.64 | 0.06358 |
| M | TS | 44 | 5 | 183 | 83.18 | 0.06011 |
| F | TS, OCD, D | 35 | 5 | 131 | 59.55 | 0.08397 |
| M | TS | 18 | 2.5* | 152 | 69.09 | 0.036 |
| M | ADHD, TS | 16 | 7.5 | 163 | 74.09 | 0.10123 |
| M | TS | 36 | 2.5 | 155 | 70.45 | 0.03548 |
| M | ADHD, TS | 14 | 2.5 | 170 | 77.27 | 0.03235 |
| M | TS | 23 | 2.5 | 146 | 66.36 | 0.03767 |
| F | TS, OCD, D | 16 | 2.5 | 125+ | 56.81 | 0.044 |

*While 2.5 mg/day effectively controlled hand tremors in this patient, reducing the daily dose to 1.25 mg/day resulted in a return of tremors.
+Estimated

TABLE 2

Estimated Therapeutic Dose Ranges According to Body Weight

| Body Weight | Daily Therapeutic Dosage Range* (mg) | |
|---|---|---|
| (lbs) | Low dose (mg) | High dose (mg) |
| 55 | 0.75 | 2.5 |
| 75 | 1 | 3.5 |
| 95 | 1.25 | 4.5 |
| 115 | 1.75 | 5 |
| 135 | 2 | 5.5 |
| 155 | 2.25 | 6.5 |
| 175 | 2.5 | 7.5 |
| 195 | 2.75 | 8.5 |
| 215 | 3 | 9.5 |

*Based on the tested range of 0.03–0.10 mg/kg

The foregoing description and examples are intended only to illustrate, not limit, the disclosed invention.

We claim:

1. A method of treating cognitive deficits in learning and memory in individuals in need thereof, the method comprising administering to the individual an effective amount of a mecamylamine or a mecamylamine stereoisomer.

2. The method of claim 1 wherein the mecamylamine or mecamylamine stereoisomer is dimethylamino mecamylamine.

3. The method of claim 1, wherein the effective amount of the mecamylamine or mecamylamine stereoisomer is 0.005–1.00 mg/kg/day.

4. The method of claim 1 in which the cognitive deficits in learning and memory are brought on by therapy using conventional neuroleptic drugs.

5. The method of claim 1 additionally comprising administration of an atypical neuroleptic drug.

6. A method of treating cognitive deficits in learning and memory associated with learning disorders in individuals in need thereof, the method comprising administering to the individual an effective amount of mecamylamine or mecamylamine stereoisomer.

7. The method of claim 6, wherein the mecamylamine or mecamylamine stereoisomer is dimethylamino mecamylamine.

8. The method of claim 6, wherein the effective amount of the mecamylamine or mecamylamine stereoisomer is 0.005–1.00 mg/kg/day.

9. A method of treating cognitive deficits in learning and memory associated with age-related cognitive disorders in an individual in need thereof, the method comprising administering to the individual an effective amount of a mecamylamine or a mecamylamine stereoisomer.

10. The method of claim 9, wherein the mecamylamine or mecamylamine stereoisomer is dimethylamino mecamylamine.

11. The method of claim 9, wherein the effective amount of the mecamylamine or mecamylamine stereoisomer is 0.005–1.00 mg/kg/day.

12. The method of claim 9 in which the cognitive deficits in learning and memory are caused or exacerbated by therapy using conventional neuroleptic drugs.

13. The method of claim 9 additionally comprising administering an atypical neuroleptic drug.

14. The method of claim 1, wherein the effective amount is from about 0.001 mg/kg/day to about 10 mg/kg/day.

15. The method of claim 1, wherein the effective amount is from about 0.002 mg/kg/day to about 7 mg/kg/day.

16. The method of claim 1, wherein the effective amount is from about 0.005 mg/kg/day to about 2 mg/kg/day.

17. The method of claim 1, wherein the effective amount is from about 0.005 mg/kg/day to about 10 mg/kg/day.

18. The method of claim 1, wherein the effective amount is from about 0.01 mg/kg/day to about 1.5 mg/kg/day.

19. The method of claim 1, wherein the effective amount is from about 0.01 mg/kg/day to about 0.5 mg/kg/day.

20. The method of claim 1, wherein the effective amount is from about 0.03 mg/kg/day to about 0.1 mg/kg/day.

21. The method of claim 1, wherein the mecamylamine or mecamylamine stereoisomer is administered in a sustained or delayed release dosage form.

22. The method of claim 1, wherein the mecamylamine or mecamylamine stereoisomer is administered by bronchial inhalation.

23. The method of claim 6, wherein the effective amount is from about 0.001 mg/kg/day to about 10 mg/kg/day.

24. The method of claim 6, wherein the effective amount is from about 0.002 mg/kg/day to about 7 mg/kg/day.

25. The method of claim 6, wherein the effective amount is from about 0.005 mg/kg/day to about 2 mg/kg/day.

26. The method of claim 6, wherein the effective amount is from about 0.005 mg/kg/day to about 10 mg/kg/day.

27. The method of claim 6, wherein the effective amount is from about 0.01 mg/kg/day to about 1.5 mg/kg/day.

28. The method of claim 6, wherein the effective amount is from about 0.01 mg/kg/day to about 0.5 mg/kg/day.

29. The method of claim 6, wherein the effective amount is from about 0.03 mg/kg/day to about 0.1 mg/kg/day.

30. The method of claim 6, wherein the mecamylamine or mecamylamine stereoisomer is administered in a sustained or delayed release dosage form.

31. The method of claim 6, wherein the mecamylamine or mecamylamine stereoisomer is administered by bronchial inhalation.

32. The method of claim 9, wherein the effective amount is from about 0.001 mg/kg/day to about 10 mg/kg/day.

33. The method of claim 9, wherein the effective amount is from about 0.002 mg/kg/day to about 7 mg/kg/day.

34. The method of claim 9, wherein the effective amount is from about 0.005 mg/kg/day to about 2 mg/kg/day.

35. The method of claim 9, wherein the effective amount is from about 0.005 mg/kg/day to about 10 mg/kg/day.

36. The method of claim 9, wherein the effective amount is from about 0.01 mg/kg/day to about 1.5 mg/kg/day.

37. The method of claim 9, wherein the effective amount is from about 0.01 mg/kg/day to about 0.5 mg/kg/day.

38. The method of claim 9, wherein the effective amount is from about 0.03 mg/kg/day to about 0.1 mg/kg/day.

39. The method of claim 9, wherein the mecamylamine or mecamylamine stereoisomer is administered in a sustained or delayed release dosage form.

40. The method of claim 9, wherein the mecamylamine or mecamylamine stereoisomer is administered by bronchial inhalation.

41. A method for treating cognitive deficits in learning and memory in a patient suffering from executive dysfunction, the method comprising administering an effective amount of mecamylamine or a mecamylamine stereoisomer.

42. The method of claim 41, wherein the effective amount is from about 0.001 mg/kg/day to about 10 mg/kg/day.

43. The method of claim 41, wherein the effective amount is from about 0.002 mg/kg/day to about 7 mg/kg/day.

44. The method of claim 41, wherein the effective amount is from about 0.005 mg/kg/day to about 2 mg/kg/day.

45. The method of claim 41, wherein the effective amount is from about 0.005 mg/kg/day to about 10 mg/kg/day.

46. The method of claim 41, wherein the effective amount is from about 0.01 mg/kg/day to about 1.5 mg/kg/day.

47. The method of claim 41, wherein the effective amount is from about 0.01 mg/kg/day to about 0.5 mg/kg/day.

48. The method of claim 41, wherein the effective amount is from about 0.03 mg/kg/day to about 0.1 mg/kg/day.

49. The method of claim 41, wherein the mecamylamine or mecamylamine stereoisomer is administered in a sustained or delayed release dosage form.

50. The method of claim 41, wherein the mecamylamine or mecamylamine stereoisomer is administered by bronchial inhalation.

51. A method for treating cognitive deficits in learning and memory in a patient suffering from attention deficit hyperactivity disorder, the method comprising administering an effective amount of a mecamylamine or a mecamylamine stereoisomer.

52. The method of claim 51, wherein the effective amount is from about 0.001 mg/kg/day to about 10 mg/kg/day.

53. The method of claim 51, wherein the effective amount is from about 0.002 mg/kg/day to about 7 mg/kg/day.

54. The method of claim 51, wherein the effective amount is from about 0.005 mg/kg/day to about 2 mg/kg/day.

55. The method of claim 51, wherein the effective amount is from about 0.005 mg/kg/day to about 10 mg/kg/day.

56. The method of claim 51, wherein the effective amount is from about 0.01 mg/kg/day to about 1.5 mg/kg/day.

57. The method of claim 51, wherein the effective amount is from about 0.01 mg/kg/day to about 0.5 mg/kg/day.

58. The method of claim 51, wherein the effective amount is from about 0.03 mg/kg/day to about 0.1 mg/kg/day.

59. The method of claim 51, wherein the mecamylamine or mecamylamine stereoisomer is administered in a sustained or delayed release dosage form.

60. The method of claim 51, wherein the mecamylamine or mecamylamine stereoisomer is administered by bronchial inhalation.

61. A method for treating cognitive deficits in learning and memory in a patient suffering from bipolar disorder, the method comprising administering an effective amount of a mecamylamine or a mecamylamine stereoisomer.

62. The method of claim 61, wherein the effective amount is from about 0.001 mg/kg/day to about 10 mg/kg/day.

63. The method of claim 61, wherein the effective amount is from about 0.002 mg/kg/day to about 7 mg/kg/day.

64. The method of claim 61, wherein the effective amount is from about 0.005 mg/kg/day to about 2 mg/kg/day.

65. The method of claim 61, wherein the effective amount is from about 0.005 mg/kg/day to about 10 mg/kg/day.

66. The method of claim 61, wherein the effective amount is from about 0.01 mg/kg/day to about 1.5 mg/kg/day.

67. The method of claim 61, wherein the effective amount is from about 0.01 mg/kg/day to about 0.5 mg/kg/day.

68. The method of claim 61, wherein the effective amount is from about 0.03 mg/kg/day to about 0.1 mg/kg/day.

69. The method of claim 61, wherein the mecamylamine or mecamylamine stereoisomer is administered in a sustained or delayed release dosage form.

70. The method of claim 61, wherein the mecamylamine or mecamylamine stereoisomer is administered by bronchial inhalation.

* * * * *

UNITED STATES PATENT AND TRADEMARK OFFICE
CERTIFICATE OF CORRECTION

PATENT NO.       : 6,979,698 B1
APPLICATION NO.  : 09/526403
DATED            : December 27, 2005
INVENTOR(S)      : Sanberg et al.

It is certified that error appears in the above-identified patent and that said Letters Patent is hereby corrected as shown below:

Title Page
At # 75, the spelling of the inventor's surname should be corrected as follows:

Paul R. Sanberg

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,979,698 B1 Page 1 of 1
APPLICATION NO. : 09/526403
DATED : December 27, 2005
INVENTOR(S) : Sanberg et al.

It is certified that error appears in the above-identified patent and that said Letters Patent is hereby corrected as shown below:

Title Page item (73)

At Paragraph 73, the Assignee should be corrected as follows:

University of South Florida, Tampa, Florida

Signed and Sealed this

Sixth Day of November, 2007

JON W. DUDAS
*Director of the United States Patent and Trademark Office*